United States Patent [19]

Herdeman

[11] Patent Number: 4,707,287

[45] Date of Patent: Nov. 17, 1987

[54] DRY BLEACH STABLE ENZYME COMPOSITION

[75] Inventor: Robert W. Herdeman, Loveland, Ohio

[73] Assignee: The Procter & Gamble Company, Cincinnati, Ohio

[21] Appl. No.: 750,715

[22] Filed: Jun. 28, 1985

[51] Int. Cl.[4] .......... C11D 3/386; C11D 3/39; C12N 9/96; C12N 9/98

[52] U.S. Cl. .......... 252/91; 252/89.1; 252/95; 252/99; 252/135; 252/174.12; 252/174.13; 252/174.14; 252/174.21; 252/DIG. 12; 252/188.1; 427/213; 427/214; 427/220; 435/188

[58] Field of Search .......... 252/89.1, 95, 99, 135, 252/174.12, 174.13, 174.21, 174.24, 174.14, DIG. 12, 91; 435/188; 427/213, 214, 220

[56] References Cited

U.S. PATENT DOCUMENTS

| | | | |
|---|---|---|---|
| 2,676,138 | 4/1954 | Hinkel | 435/188 |
| 3,117,027 | 1/1964 | Lindlof et al. | 118/383 |
| 3,196,827 | 7/1965 | Wurster et al. | 118/24 |
| 3,451,935 | 6/1969 | Roald et al. | 252/135 |
| 3,519,570 | 7/1970 | McCarty | 252/135 |
| 3,634,266 | 1/1972 | Theile | 252/132 |
| 3,637,509 | 1/1972 | Brennan | 252/99 |
| 3,650,961 | 3/1972 | Hudson | 252/99 |
| 3,691,090 | 9/1972 | Kitajima et al. | 252/316 |
| 3,723,327 | 3/1973 | van Kampen et al. | 252/110 |
| 3,741,901 | 6/1973 | Ziffer | 435/188 |
| 3,784,476 | 1/1974 | van Kampen et al. | 252/109 |
| 3,944,497 | 3/1976 | Alterman | 252/96 |
| 3,975,280 | 8/1976 | Hachmann et al. | 252/102 |
| 4,009,076 | 2/1977 | Green et al. | 195/63 |
| 4,016,041 | 4/1977 | van Kampen | 195/68 |
| 4,100,151 | 7/1978 | Adler-Nissen | 260/112 |
| 4,106,991 | 8/1978 | Markussen et al. | 195/63 |
| 4,219,436 | 8/1980 | Gromer et al. | 252/135 |
| 4,381,247 | 4/1983 | Makagawa | 252/95 |
| 4,403,994 | 9/1983 | Hignett | 8/111 |
| 4,417,994 | 11/1983 | Stoddart | 252/135 |
| 4,455,249 | 6/1984 | Broze | 252/95 |
| 4,473,507 | 9/1984 | Bossu | 260/502 R |

FOREIGN PATENT DOCUMENTS 59-204697 11/1984 Japan .

OTHER PUBLICATIONS

T-Granulate—Technical Bulletin, "Novo Enzymes," Mar. 1982, Novo Industri A/S.

*Primary Examiner*—Dennis L. Albrecht
*Attorney, Agent, or Firm*—Leonard Williamson; Richard C. Witte

[57] ABSTRACT

This invention relates to an improved granulate enzyme composition comprising a core of enzyme material and a protective coating comprising alkaline buffer salt. The improved granulate enzyme composition has improved stability when mixed with a dry peroxyacid bleach granulate.

24 Claims, 2 Drawing Figures

DRY BLEACH STABLE ENZYME COMPOSITION

BACKGROUND OF THE INVENTION

This invention relates to an improved granulate enzyme composition and to a process for making same. The improved granulate enzyme composition has improved stability when mixed with a peroxyacid bleach granulate.

During the last score of years the use of enzymes, especially of microbial origin, has been more and more common. Enzymes are used in, for example, the starch industry to produce glucose and fructose by means of amylases, amylglucosidases and glucose isomerases. In the dairy industry a vast tonnage of rennets is used and in the detergent industry proteases are normally used as additives in the washing powders to impart a better action on proteinaceous stains on the laundry.

On July 7, 1970, C. B. McCarty was granted U.S. Pat. No. 3,519,570 for enzyme-containing detergent compositions and a process for conglutination of enzymes and detergents.

U.S. Pat. No. 3,784,476, van Kampen et al., issued Jan. 8, 1974, discloses a particulate enzyme-containing detergent composition containing a detergent surface-active agent, a water-soluble builder salt and discrete, shaped inorganic solids containing proteolytic or amylolytic enzymes. It should be noted that this patent does not teach an enzyme core coated with an alkaline buffer salt as disclosed herein.

U.S. Pat. No. 4,106,991, Markensen et al., issued Aug. 15, 1978, incorporated herein in its entirety, discloses an improved formation for enzyme granulates through inclusion within the composition of finely divided cellulose fibers. Optionally a waxy substance can be employed for the granulating agent, or to coat the granulate. This patent claims a granulate composition comprising enzyme, inorganic salts, a granulation binder, and finely divided cellulose fibers as 2–40% by weight of the granulate.

Making a storage stable mixture of enzyme containing granulates and dry peroxyacid bleach granulates is a difficult task. In spite of the fact that some commercially available enzyme granulates are advertised as "perborate bleach stable," they are weak storagewise in the presence of strong peroxyacid bleach granulates. It should be noted that peroxyacid bleach granulates are relative newcomers to the dry commercial laundry detergent and bleach markets. The term "bleach" as used herein unless otherwise specified means peroxyacid bleach and the terms "peroxyacid bleach powder" and "peroxyacid bleach granulates" are synonymous unless otherwise specified.

SUMMARY OF THE INVENTION

This invention relates to an improved granulate enzyme composition comprising a core of enzyme material and a protective coating comprising alkaline buffer salt. In another respect this invention relates to a process for making the improved granulate enzyme composition comprising coating an enzyme core material with an alkaline buffer salt protective coating. The improved granulate enzyme composition is stable when mixed with peroxyacid bleach granulates.

OBJECTS

Figure 1:
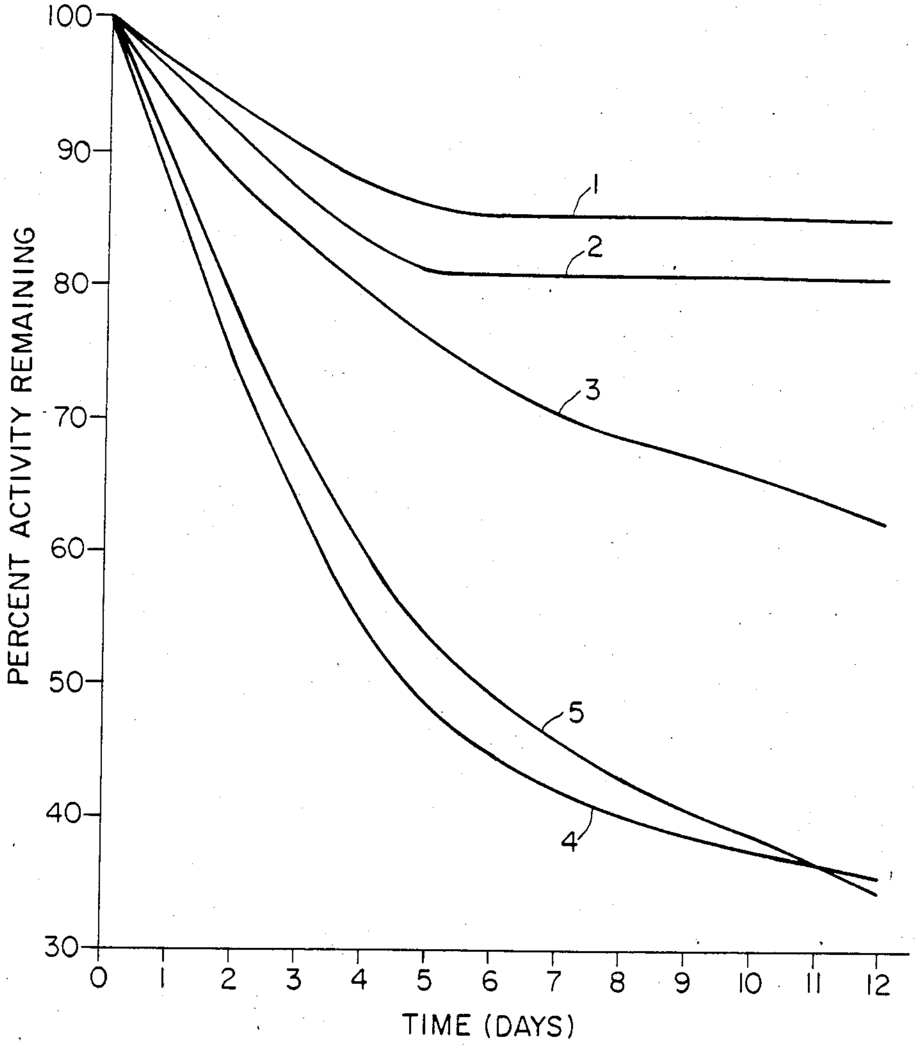
FIGS. 1 and 2 are graphs illustrating the stability of compositions of the present invention vs. various coated and uncoated enzyme granulate materials in the presence of a dry peroxyacid bleach granulate composition.

An object of the present invention is to provide an improved granulate enzyme composition which can be mixed with a peroxyacid granulate and stored without rapid loss of enzyme activity. Other objects will be apparent in the light of this disclosure.

DETAILED DESCRIPTION OF THE INVENTION

This invention relates to an improved water-soluble granulate enzyme composition comprising an enzyme core containing enzymes, fillers and/or binders and a substantially enzyme-free protective coating of alkaline buffer salt surrounding said core. The alkaline buffer salt protective coating is applied substantially completely around the enzyme core. The alkaline buffer salt protective coating preferably contains from 50–100% of said alkaline buffer salt. The remainder being selected from antioxidants, calcium chloride, and other compatible inorganic salts. The alkaline buffer salt coating has a pH of from about 7 to about 11. The practical level of alkali buffer salt protective coating is from about 10% to about 100% by weight of the core, but can be less than 10% or greater than 100%. The key is substantially surrounding the core with an effective amount of alkaline buffer salt to protect the enzyme from deactivation when mixed with dry peroxyacid bleach granulates. When factored into the total composition the 10–100% becomes about 5–50% of the alkaline buffer salt itself. Some practical ratio levels of enzyme core to coating, overcoating and encapsulating material (defined below) are from 10:1 to 0.5:1, preferably 4:1 to 1:1, and more preferably about 1.5:1.

The percentages used herein are by weight of the total composition unless otherwise specified.

The improved granulate enzyme composition on a total composition weight percentage basis preferably comprises:

- from 33% to 90%, more preferably from about 50% to about 80%, enzyme core containing enzyme powder and material selected from cellulosic fillers, binders and inorganic salt fillers, and mixtures thereof;
- from 5% to 67%, more preferably 10% to 45%, alkaline buffer salt in the protective coating surrounding said core; said protective coating including from 0.5% to 62%, more preferably 2% to 30%, of an antioxidant in the coating surrounding said core;
- from 5% to 57%, more preferably 10% to 30%, water-soluble nonionic waxy overcoating;
- from 5% to 57%, more preferably 10% to 30%, alkaline solution soluble acetate phthalate resin cap.

In the compositions of this invention, the alkaline buffer salt and antioxidant are coated on the enzyme core prior to overcoating with waxy and/or said resin cap.

The improved granulate enzyme composition preferably is made with an enzyme powder level of from about 1% to about 20% (0.5 to 10 Au/gram), and more preferably from about 1% to about 10% (0.5 to 5 Au/-gram) by weight of the total composition. The filler and binder in the core can have a ratio of from 10:1 to 1:1. A practical level of cellulosic fillers in the total composition can be from about 2% to about 36%. Au equals Anson units and is a term commonly used in the trade of describe enzyme activity.

As shown in FIG. 1, the stability of the alkaline buffer salt coated granulate enzyme composition of this invention is further improved with the addition of an antioxidant to the protective coating. The antioxidant is preferably used in the protective coating at a level of from 1% to 40%, more preferably 2% to 30% by weight of the total composition. It is preferably applied with the alkaline buffer salt, but can be applied separately. As shown in FIG. 1, the granulate enzyme composition of this invention is further improved if it has an overcoat of water-soluble nonionic waxy material. Such an overcoat is preferably used at a level of 10% to 30% and more preferably 15% to 25% of the total composition.

The improved granulate enzyme compositions of this invention can be mixed with the other laundry active powders including peroxyacid bleaches, softeners, detergents, etc. Examples of powdered detergent materials are disclosed in U.S. Pat. No. 4,404,128, B. J. Anderson, issued Sept. 13, 1983, incorporated herein by reference. Examples of powdered peroxyacid bleach granulates are disclosed in U.S. Pat. No. 4,473,507, F. P. Bossu, issued Sept. 25, 1984, incorporated herein by reference.

A preferred mixture is an enzyme-peroxyacid bleach granulate mixture comprising the alkaline buffer salt protective coated enzyme granulate of this invention and a peroxyacid bleach granulate having a weight ratio of from 1:1 to 1:1500 of coated enzyme granulates to bleach granulates, preferably 1:3 to 1:30. Details of such a preferred mixture is disclosed below.

The Alkaline Buffer Salt

The term "alkaline buffer salt" as used herein means a salt having a pH of 7–11 and which provides a comparable pH for the alkaline buffer salt protective coating in the presence of acidic substances for an extended period of time. Thus, the alkaline buffer salt useful in the present invention can be any one of a number of suitable compatible inorganic salts which have a pH of 7–11. A pH of 8–10 is preferred. The pH of a salt is measured as a 10% aqueous solution of the salt. Some preferred alkaline buffer salts are potassium bicarbonate, potassium carbonate, tetrapotassium pyrophosphate, potassium tripolyphosphate, sodium bicarbonate and sodium carbonate. Other suitable alkaline buffer salts can be used.

The alkaline buffer salt can constitute 100% of the protective coating. However, other compatible materials can be included, e.g., other inorganic salts, fillers, binders, etc. An aqueous solution of the protective coating ingredients can be used to apply the protective coating to the enzyme core. Preferably, the solution will contain 170–300 ppm calcium as calcium chloride in addition to the other protective coating ingredients.

The Antioxidant

As used herein the term "antioxidant" means a substance that opposes oxidation or inhibits reaction provided by oxygen or peroxides. The antioxidant is a stability booster for the alkaline buffer salt coating. The antioxidant increases the stability of the enzyme when used in conjunction with alkaline buffer salt.

The preferred enzyme granulate protective coating can contain 0.5% to 62% of an antioxidant inorganic salt, preferably from 1–40%, and more preferably 2–30%. The protective coating, however, must have an effective amount of alkaline buffer salt present therein. Some preferred antioxidant salts are sodium sulfite, sodium bisulfite and sodium thiosulfate. Other suitable antioxidant salts can also be used.

The Alkaline Buffer Salt Process for Coating of the Core

The enzyme core used in the present invention can be coated by any number of known apparatuses. Coating in a fluidized bed is preferred. Examples of suitable apparatuses and processes are disclosed in U.S. Pat. Nos. 3,196,827, Wurster and Lindlof, issued July 27, 1965; 3,253,944, Wurster, issued May 31, 1966; and 3,117,027, Lindlof and Wurster, issued Jan. 7, 1964, all incorporated herein by reference.

U.S. Pat. No. 3,117,027 discloses a preferred fluidized bed apparatus which can be used for coating the small enzyme core particles used in the present invention. The fluidized bed will provide substantially uniformly enzyme coated granulates.

The alkaline buffer salt process for coating the core comprises:

1. Forming an enzyme core granulate having a particle size of from 100 to 1600μ, preferably 200 to 800μ, with or without an optional waxy coating. Alternatively, an enzyme core can be provided.

2. Coating the enzyme core with an effective amount of alkaline buffer salt coating, preferably at a level of from about 10% to about 100% by weight of the core on a dry weight basis. The core should be surrounded by the coating and the coating should contain an effective amount of alkaline buffer salt.

The protective coating is preferably applied to the enzyme core as a 15% to 70% (preferably 20% to 50%) solids aqueous solution in a fluidized bed. The temperature range of the solution can be about 60°–82° C. (140°–180° F.), and is preferably about 65°–77° C. (150°–170° F.). The air temperature of the fluidized bed is 45° to 77° C. for the coating/drying operation. The rate of addition of the coating solution and the rate of drying are dependent on the solution concentration, temperature of air, volume, etc.

Calcium Present in the Coating

The granulate enzyme composition of this invention can be improved if it contains from about 40 to 3000 ppm of calcium, calculated as calcium chloride. Calcium can be added to the granulate by using water containing a calcium content of 100–500 ppm, preferably 170–300 ppm, calculated as calcium chloride in the protective coating solution.

The 24 Day Storage test results shown in Table 1 show that the Sample B made with water of 10–16 grain hardness is more stable than Sample A made with deionized water. The Sample B contains about 500 ppm to about 1000 ppm of added calcium chloride.

TABLE 1

24 Days Storage at 100° F. (38° C.)

| | Coating | % Enzyme Activity Remaining |
|---|---|---|
| Sample A: | $KHCO_3/Na_2SO_3/TAE_{22}$ with salt applied with deionized water | 67% |
| Sample B: | $KHCO_3/Na_2SO_3/TAE_{22}$ with salt applied with "city water" at 10–16 grain hardness | 85% |

Samples A and B are similar to Composition 1 of Table 3 and thus are identical but for the coating solution water. $TAE_{22}$ is tallow alcohol condensed with 22 ethylene oxide moles per mole of alcohol.

The Enzyme Core

The enzyme core used in the present invention is a smaller granulate than the coated one. The core has a particle size of from 100 to 1600μ, preferably from about 200 to about 800μ, more preferably 300–400μ. A commercially available enzyme core is the "T-Granulate" available from NOVO Industri A/S, Bagsvard, Denmark.

A preferred enzyme core granulate and process for making same are generally disclosed in U.S. Pat. No. 4,106,991, Markensen et al., issued Aug. 15, 1978, incorporated herein in its entirety. The process comprises drum granulating an enzyme composition including inorganic salts, and a granulation binder, with a liquid phase granulating agent, and finely divided cellulose fibers in an amount of 2–40% w/w based upon the dry weight of the total composition.

As reported in said Markensen et al.'s patent, supra, more specifically, the process for the production of enzyme core granulates comprises the introduction into drum granulator of from 2 to 40% by weight of cellulose in fibrous form, from 0 to 10% by weight of a binder as herein defined, enzyme and filler in an amount which generates the intended enzyme activity in the finished granulate, a liquid phase granulating agent consisting of a waxy substance, as defined herein, and/or water, in an amount of between 5 and 70% by weight, whereby the maximum amount of waxy substance is 40% by weight and the maximum amount of water is 70% by weight, whereby all percentages are referring to the total amount of dry substances, the sequence of the introduction of the different materials being arbitrary, except that at least a major part of the granulating agent is introduced after at least a substantial part of the dry substances is introduced in the granulator, whereafter the granulate, if necessary, if dried in a conventional manner, preferably in a fluid bed.

The granulates so produced are reported by Markensen et al., supra, to have a higher physical stability and a higher resistance against abrasion than granulates without cellulose fibers and, consequently, a very low dust level. They are excellent enzyme core granulates for the present invention.

The cellulose in fibrous form can be sawdust, pure, fibrous cellulose, cotton, or other forms of pure or impure fibrous cellulose.

Several brands of cellulose in fibrous form are on the market, e.g., CEPO and ARBOCEL. In a publication from Svenska Tramjolsfabrikerna AB, "Cepo Cellulose Powder," it is stated that for Cepo S/20 cellulose the approximate minimum fiber length is 500μ, the approximate average fiber length is 160μ, the approximate maximum fiber width is 50μ and the approximate average fiber width is 30μ. Also, it is stated that CEPO SS/200 cellulose has an approximate maximum fiber length of 150μ, an approximate average fiber length of 50μ, an approximate maximum fiber width of 45μ and an appoximate average fiber width of 25μ. Cellulose fibers with these dimensions are very well suited for the purpose of the invention.

The binders used in the process are the binders conventionally used in the field of granulation with a high melting point or with no melting point at all and of a nonwaxy nature, e.g., polyvinyl pyrrolidone, dextrina, polyvinylalcohol, and cellulose derivatives, including for example hydroxypropyl cellulose, methyl cellulose or CMC. A granulate cannot be formed on the basis of cellulose, enzyme, filler and a binder, without the use of a granulating agent, as defined below.

All enzymes can be granulated by means of said process. Preferably, amylases and proteinases are granulated according to the invention. Specific examples are ALCALASE (a Bacillus licheniformis proteinase), ESPERASE and SAVINASE (microbial alcaline proteinases produced according to British Pat. No. 1,243,784) and TERMAMYL (a Bacillus licheniformis amylase). The enzyme can be introduced into the granulator as a predried milled powder or a solution, for example, a concentrated enzyme solution prepared by ultrafiltration, reverse osmosis or evaporation.

The filler is used only for the purpose of adjusting to the intended enzyme activity in the finished granulate. Since the enzyme introduced into the granulator already contains diluent impurities which are considered as fillers, an additional filler is not always needed to standardize the enzymatic activity of the granulate. A preferred filler for the core can be an alkaline buffer salt or an antioxidant inorganic salt or mixtures thereof as defined herein.

The granulating agent is water and/or a waxy substance. The granulating agent is always used as a liquid phase in the granulation process; the waxy substance if present therefore is either dissolved or dispersed in the water or melted. By a "waxy substance" is understood a substance which possesses all of the following characteristics: (1) the melting point is between 30° and 100° C., preferably between 40° and 60° C., (2) the substance is of a tough and not brittle nature, and (3) the substance possesses substantial plasticity at room temperature.

Both water and waxy substances are granulating agents, i.e., they are both active during the formation of the granulate cores; the waxy substance stays as a constituent in the finished granulate cores, whereas the majority of the water is removed during the drying. Thus, in order to refer all amounts to be finished, dry granulate cores, all percentages are calculated on the basis of total dry cores, which means that water, one of the granulating agents, is not added to the other constituents when calculating the percentage of water, whereas the waxy substance, the other core granulating agent, has to be added to the other dry constituents when calculating the percentage of waxy substance. Examples of waxy substances are polyglycols, fatty alcohols, ethoxylated fatty alcohols, higher fatty acids, mono-, di- and triglycerolesters of higher fatty acids, e.g., glycerol monostearate, alkylarylethoxylates, and coconut monoethanolamide.

An illustrative summary of a process used to make an enzyme granulate core is:

1. Provide dry enzyme powder fillers, binders, etc.
2. Mix the dry powders of the core composition.
3. Wet the powder mixture with granulating agent, e.g., water or waxy melt.
4. Process the wet powder mixture of Step 3 in a granulating apparatus (e.g., rotating knife) to form a granulate core having the desired particle size distribution.

A cylindrical Lodige type mixer FM 130 DIZ (U.S. Pat. No. 3,027,102) can be used in the process for this step. The mixer is equipped with both plough shaped mixers mounted on a horizontal (axial) rotating shaft and a granulating device, consisting of one or more cross knives mounted on a shaft introduced into the mixer through the cylindrical wall in a direction perpendicular to the abovementioned horizontal rotating shaft (i.e., radial of the cylinder).

5. Dry in a fluidized bed the moist granulate core of Step 4 until a dryness which satisfies both the requirements of enzyme stability and the requirements of free-flowing properties and mechanical strength. Usually this will correspond to a water content less than 10%, preferably less than 3% and more preferably bone dry. In the instances where the granulating agent is exclusively or principally a waxy substance only cooling may be required.

6. In an optional sixth step, the granulate of Step 5 can be coated with a waxy or some other compatible substance.

The core is then coated with alkaline buffer salt.

Some preferred enzyme core granulate compositions and component ranges are set out in Table 2.

TABLE 2

| Ingredient | Enzyme Core Granulate Levels Preferred | Low | High |
|---|---|---|---|
| Proteolytic Enzyme | 4 | 0.5 | 15 |
| Amylase Enzyme | 1 | 0 | 3 |
| Ca Sulfate, $CaCl_2$ / Na Sulfate, NaCl | 45 | 3.0 | 97.5 |
| Cellulose Filler & Binder | 25 | 2.0 | 40 |
| Waxy Overcoat (PEG 1500) | 25 | 0 | 40 |

Such enzyme cores constitute from 33% to 90% by weight of the preferred and practical coated compositions of this invention.

Optional Waxy Coating Material

A nonionic waxy material can be applied over the core or over the alkaline buffer salt coated enzyme granulate. The practical levels of waxy "overcoats" are up to 57% by weight of the composition, preferably 5-30%, and more preferably 15-25%. The term "overcoat" as used herein means over the alkaline buffer salt coating including mixture of alkaline buffer salt and antioxidant salt. Examples of such waxy overcoatings are polyethylene glycols, fatty alcohols, ethoxylated fatty alcohols, higher fatty acids, mono-, di- and triglycerolesters of fatty acids, e.g., glycerol monostearate, alkylarylethoxylates and coconut monoethanolamide. Preferred nonionic waxy substances are $TAE_{22}$ (tallow alcohol condensed with 22 moles of ethylene oxide per mole of alcohol), PEG 1500–8000 (polyethylene glycol of molecular weight 1500–8000) and palmitic acid. Other waxy coatings having a melting point of at least 38° C., preferably at least 50° C., can also be used. For example, this waxy coating is melted (50°–70° C.) and is sprayed onto the granulate in a fluidized bed where cool air (15°–30° C.) is applied to solidify the waxy coating.

The Figures

Figure 2:
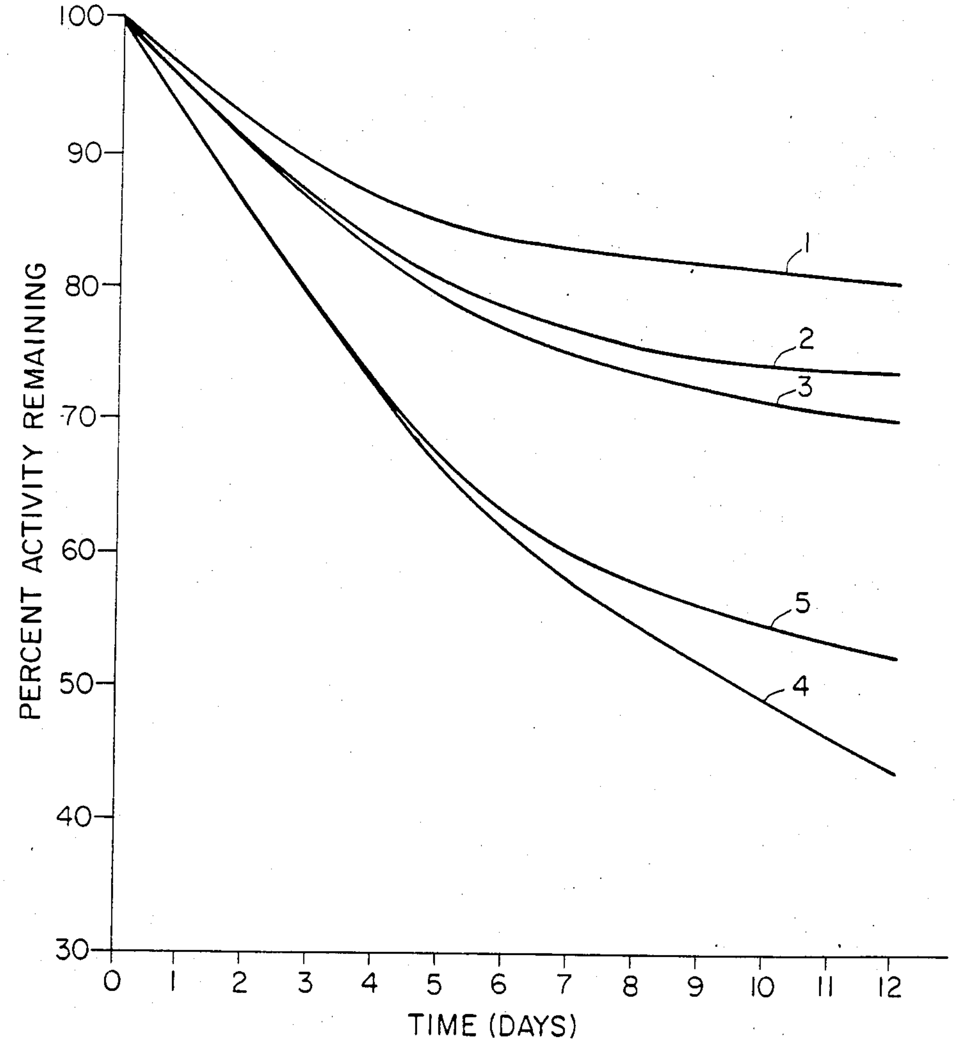

FIGS. 1 and 2 show potent graphical illustrations of the improved stability of the alkaline buffer salt coated granulate enzyme compositions of the present invention over some other granulate enzyme compositions. The enzyme granulate compositions 1–5 of Table 3 correspond to Curves 1–5 in FIGS. 1 and 2. The levels of ingredients reported in Table 3 as percentages of the total granulate enzyme composition. The coating procedure used to make compositions 1–3 and 5 is set out in Example II.

TABLE 3

| Curve Coating | Enzyme Granulate Compositions 1 % | 2 Wt % | 3 Wt % | 4 Wt % | 5 Wt % |
|---|---|---|---|---|---|
| (T-Granulate) | 61.5 | 61.5 | 80 | 100 | 80 |
| Potassium Bicarbonate | 15.4 | 18.5 | 20 | — | — |
| Sodium Bisulfite | 3.1 | — | — | — | — |
| $TAE_{22}$ | 20.0 | 20.0 | — | — | 20 |

Four grams of each composition (1–5) of Table 3 were mixed with 20 grams of the peroxyacid bleach composition of Example III. Referring to FIG. 1, stability tests were conducted at about 100° F. (38° C.) and ambient humidity. Referring to FIG. 2, the stability tests were conducted at 80° F. (27° C.) and 15% relative humidity. In both tests the Enzyme Stability (ES) Curve 1 is the best. Thus, Composition 1 of Table 2 represents a potent embodiment comprising an alkaline buffer salt/antioxidant coated granulate enzyme composition with an overcoat of $TAE_{22}$ in the presence of peroxyacid bleach as set out in Example II. Enzyme Stability (ES) Curve 2 shown in FIGS. 1 and 2 is the next best. Note that Composition 2 of Table 3 is the same as Composition 1, but without the antioxidant. ES Curve 3 is the same as "2" without the overcoat, $TAE_{22}$.

ES Curve 4 is a prior art overcoat T-Granulate and ES Curve 5 is a prior art T-Granulate with additional $TAE_{22}$ overcoating.

Similar potent stability results were obtained at a lower temperature (27° C.) and 15% relative humidity as shown in FIG. 2.

EXAMPLE I

A preferred enzyme core can be made using the procedure outlined above using the following ingredients:

| Ingredinet | Wt % |
|---|---|
| Proteolytic Enzyme | 4 |
| Amylase Enzyme | 1 |
| Ca Sulfate, $CaCl_2$ / Na Sulfate, NaCl | 45 |
| Cellulose Filler[1] | 20 |
| Binder[2] (polyvinyl pyrrolidone) | 5 |
| Waxy Overcoat (PEG 1500) | 25 |

[1]Cellulose Powder - CEPO S20
[2]Selected from polyvinyl pyrrolidone, dextrin, polyvinyl alcohols and cellulose derviatives.

EXAMPLE II

A 6 inch Wurster Fluidized Bed Coating Unit with a capacity of about 1 liter was used. The preparation of the coated enzyme is as follows: 800 grams of enzyme T-Granulates are added to the fluid bed dryer. To this a 1,000 gram 70° C. aqueous solution, containing 200 grams of potassium bicarbonate and 40 grams of sodium sulfite, is sprayed on. The coated granulate enzyme composition is then dried at a fluid bed temperature of 75° C. to contain less than 0.5% water. The coated granulate enzyme is then removed from the fluid bed dryer and weighed to confirm coating level.

800 grams of the alkaline buffer salt/antioxidant salt-coated granulate enzyme were then placed back into the fluid bed dryer. To this 200 grams of $TAE_{22}$ were sprayed on at 55° C. and allowed to cool in the dryer with air temperature 20° C.

| Final weight %: | | |
|---|---|---|
| Enzyme T-Granulate Core | | 61.54% |
| Coating: | | |
| Potassium Bicarbonate | 15.38 | 18.46 |
| Sodium Sulfite | 3.08 | |
| $TAE_{22}$ Overcoating | | 20.00 |
| Total | | 100.00% |

The ratio of enzyme core to coating is about 3.3 to 1. The pH of the coating is 8.5.

The coated enzyme of Example II is mixed with the dry peroxyacid bleach composition as set out below in Example III. Its stability was tested vs. the stability of uncoated T-Granulate, a $TAE_{22}$ coated T-Granulate, a potassium bicarbonate coated T-Granulate, and a potassium bicarbonate plus $TAE_{22}$ coated T-Granulate. These compositions are shown in Table 3 and the stability results are shown in FIGS. 1 and 2.

EXAMPLE III

The coated enzyme granualtes similar to that described in Example II are dry mixed with peroxyacid bleach granulates in the following proportions.

| | | Wt % | Grams |
|---|---|---|---|
| Peroxyacid Bleach Granulate | | 83 | 20 |
| Diperoxydo-decanedioic Acid | 20.75 | | |
| Dodecanedioic Acid | 1.85 | | |
| Boric Acid | 22.75 | | |
| $Na_2SO_4$ | 28.06 | | |
| Sodium Acid Pyrophosphate | 5.00 | | |
| $C_{13}LAS$ | 4.50 | | |
| Coated Enzyme Granulate of Example II | | 17 | 4 |
| Enzyme Core* | 10.5 | | |
| $KHCO_3$ | 2.6 | | |
| $NA_2SO_3$ | 0.5 | | |
| $TAE_{22}$ | 3.4 | | |
| | | 100 | 24 |

*Enzyme core is Novo T-Granulate with 2.0 Au/gram protease activity. Its approximate composition is shown in Example I.

The process used to made the peroxyacid bleach granulate in Example III is disclosed in U.S. Pat. No. 4,497,757, Beimesch and Hortel, issued Feb. 2, 1985, incorporated herein by reference in its entirety.

The peroxyacid bleach and enzyme granule mixture composition of Example III comprising the alkaline buffer salt protective coated enzyme granulate and a peroxyacid bleach granulate having a ratio of from 1 to 5 was storage stable for more than 10 weeks at 38° C. Thus, this invention offers an improved enzyme granulate which is storage stable with a peroxyacid bleach granulate, enabling them to be used together in a detergent or laundry additive product for combined bleaching and stain removal performance.

What is claimed is:

1. A dry peroxyacid bleach and enzyme granular mixture composition comprising an alkaline buffer salt protective coated enzyme granulate and a peroxyacid bleach granulate having a weight ratio of enzyme granulate to bleach granulate of from 1:1 to 1:1500; wherein said enzyme granulate comprises a core of enzyme material and a protective coating containing an effective amount of alkaline buffer salt surrounding said enzyme core and wherein said effective amount of alkaline buffer salt is selected from the group consisting of potassium bicarbonate, potassium carbonate, sodium bicarbonate, and mixtures thereof; and wherein said protective coating contains an antioxiant and is selected from the group consisting of sodium sulfite, sodium bisulfite and sodium thiosulfate, and mixtures thereof; and wherein said enzyme granulate is surrounded with from about 5% to about 57% of an overcoating of water-soluble nonionic wax having a melting point of at least about 38° C.

2. The composition of claim 1 wherein said core is from about 33% to about 90% by weight of said composition.

3. The composition of claim 1 or wherein said protective coating surrounding said core is at least 10% by weight of said composition and wherein said core is from about 50% to about 80% by weight of said composition.

4. The composition of claim 1 or 2 wherein said protective coating contains 50% to 100% alkaline buffer salt by weight of said protective coating.

5. The composition of claims 1 or 2 wherein said protective coating contains 50–100% alkaline buffer salt by weight of said protective coating, and wherein when said alkaline buffer salt is present at a level of from about 5% to about 10% by weight of said composition, the balance of said coating is selected from antioxidants, calcium chloride and other compatible inorganic salts.

6. The composition of claim 1 or 2 wherein said alkaline buffer salt protective coating has a pH of 8–10, said core to coating having a weight ratio of from 4:1 to 1:1.

7. The composition of claim 1 or 2 wherein antioxidant salts are present in said protective coating at a level of 1% to 40% by weight of said composition.

8. The composition of claim 7 wherein said antioxidant is present at a level of 2% to 30% by weight of said composition.

9. The composition of claim 1 or 2 wherein said protective coating is a mixture of alkaline buffer salt and antioxidant said mixture having a pH of 8 to 10.

10. The composition of claim 1 or 2 wherein said protective coating contains calcium ion as calcium chloride at a level of 40 to 3000 ppm by weight of said composition.

11. The composition of claim 1 or 2 wherein said enzyme granulate includes a nonionic overcoat having a melting point of at least 50° C.

12. The composition of claim 11 wherein said overcoat of said water-soluble nonionic wax overcoat is present at a level of 10% to 30% by weight of said composition.

13. The composition of claim 11 wherein said water-soluble nonionic wax overcoat is present at a level of 15% to 25%.

14. The composition of claim 1 wherein said nonionic wax is selected from the group consisting of: fatty alcohols, ethoxylated fatty alcohols, higher fatty acids, mono-, di- and triglycerolesters of fatty acids, e.g., glycerol monostearate, alkylarylethoxylates and coconut monoethanolamide, and mixtures thereof.

15. The composition of claim 14 wherein said nonionic wax is selected from the group consisting of: tallow alcohol condensed with 22 moles of ethylene oxide per mole of alcohol, polyethylene glycol of molecular weight 1500–8000 and palmitic acids.

16. The composition of claim 1 or 2 wherein said enzyme granulate is encapsulated in an alkaline solution-soluble acetate phthalate resin cap.

17. The composition of claim 16 wherein said enzyme granulate has a overcoat of nonionic wax under said resin.

18. The composition of claim 1 or 2 wherein said enzyme granulate is encapsulated with a 5% to 57% alkaline solution-soluble acetate phthalate resin by weight of said composition.

19. The composition of claim 1 wherein said ratio is 1:3 to 1:30.

20. The composition of claim 1 wherein said enzyme granulate is made by a process comprising the following steps:

1. Completely coating an enzyme core with from 10% to 100%, based on weight of core, of a protective alkaline buffer salt solution having a pH of from above 7 to about 11 via a 15% to 70% solution;
2. Drying said coated core of Step 1 in a fluid bed dryer to provide said improved water-soluble enzyme granulate composition;

wherein said enzyme granulate comprises from 33% to 90% of said enzyme core, and from 5% to 67% of said alkaline buffer salt on a dry weight basis.

21. The composition of claim 20 wherein the solution of Step 1 also contains an antioxidant to provide from 0 to 62% of an antioxidant coating for said improved water-soluble granulate enzyme composition.

22. The composition of claim 20 or 21 wherein said alkaline buffer salt coated granulate is overcoated with from 5% to 57% nonionic wax via an optional step in a fluid bed.

23. The composition of claim 20 or 21 wherein said solution of Step 1 contains from 170–300 ppm calcium as calcium chloride.

24. The composition of claims 21 or 22 wherein said core of Step 1 is coated with a nonionic waxy material prior to coating with said alkaline buffer salt.

* * * * *

UNITED STATES PATENT AND TRADEMARK OFFICE

CERTIFICATE OF CORRECTION

PATENT NO. : 4,707,287

DATED : November 17, 1987

INVENTOR(S) : Robert W. Herdeman

It is certified that error appears in the above-identified patent and that said Letters Patent is hereby corrected as shown below:

Title Page, Section [54], the title should read -- DRY BLEACH STABLE ENZYME COMPOSITION COMPLETELY COATED WITH AN ALKALINE BUFFER SALT --.

Col. 1, line 1, delete "DRY BLEACH STABLE ENZYME COMPOSITION" and insert -- DRY BLEACH STABLE ENZYME COMPOSITION COMPLETELY COATED WITH AN ALKALINE BUFFER SALT --.

Col. 3, line 1, delete "of" and insert -- to --.

Col. 10, line 16, in Claim 3 after "or" insert -- 2 --.

Col. 10, line 58, in Claim 14, delete "1" and insert -- 11 --.

Col. 11, line 5, in Claim 17, delete "a" and insert -- an --.

Signed and Sealed this

Fourth Day of October, 1988

Attest:

DONALD J. QUIGG

*Attesting Officer* *Commissioner of Patents and Trademarks*